(12) United States Patent
Cheatham, III et al.

(10) Patent No.: US 9,804,303 B1
(45) Date of Patent: Oct. 31, 2017

(54) SYSTEMS FOR TUNABLE NANOCUBE PLASMONIC RESONATORS AND METHODS FOR FORMING

(71) Applicant: Elwha LLC, Bellevue, WA (US)

(72) Inventors: Jesse R. Cheatham, III, Seattle, WA (US); Tom Driscoll, San Diego, CA (US); Roderick A. Hyde, Redmond, WA (US); Muriel Y. Ishikawa, Livermore, CA (US); Jordin T. Kare, San Jose, CA (US); Nathan P. Myhrvold, Medina, WA (US); Tony S. Pan, Bellevue, WA (US); Robert C. Petroski, Seattle, WA (US); David R. Smith, Durham, NC (US); Clarence T. Tegreene, Mercer Island, WA (US); Nicholas W. Touran, Seattle, WA (US); Yaroslav A. Urzhumov, Bellevue, WA (US); Charles Whitmer, North Bend, WA (US); Lowell L. Wood, Jr., Bellevue, WA (US); Victoria Y. H. Wood, Livermore, CA (US)

(73) Assignee: Elwha LLC, Bellevue, WA (US)

( * ) Notice: Subject to any disclaimer, the term of this patent is extended or adjusted under 35 U.S.C. 154(b) by 0 days.

(21) Appl. No.: 15/092,367

(22) Filed: Apr. 6, 2016

(51) Int. Cl.
*G02B 5/00* (2006.01)
*G02B 6/122* (2006.01)
(Continued)

(52) U.S. Cl.
CPC ........... *G02B 5/008* (2013.01); *G01N 21/554* (2013.01); *G02B 6/1226* (2013.01); *G02F 1/015* (2013.01);
(Continued)

(58) Field of Classification Search
CPC ....... G02B 5/008; G02B 6/1226; G02F 1/015; G02F 2203/10; G02F 2203/15; B82Y 20/00; G01N 21/55; G01N 21/554; G01N 21/557; G01N 21/6454; G01N 21/648; G01N 21/6489; G01N 21/658; H01L 27/1443; H01L 27/1446; H01L 31/02327; H01L 31/035209; H01L 31/03529; H01L 31/0475; H01L 31/056; H01L 31/06; H01L 31/062
(Continued)

(56) References Cited

U.S. PATENT DOCUMENTS

| | | | |
|---|---|---|---|
| 6,916,451 B1 * | 7/2005 | Zuppero | B01J 35/0033 136/252 |
| 7,947,210 B2 * | 5/2011 | Pham | A61F 13/2085 264/297.3 |

(Continued)

*Primary Examiner* — Loha Ben
(74) *Attorney, Agent, or Firm* — Foley & Lardner LLP

(57) ABSTRACT

The present disclosure is directed to systems for tuning nanocube plasmonic resonators and methods for forming tunable plasmonic resonators. A tunable plasmonic resonator system can include a substrate and a nanostructure positioned on a surface of the substrate. The substrate can include a semiconductor material having a carrier density distribution. A junction can be formed between the nanostructure and the substrate forming a Schottky junction. Changing the carrier density distribution of the semiconductor material can change a plasmonic response of the plasmonic resonator.

35 Claims, 8 Drawing Sheets

(51) Int. Cl.
  *B82Y 20/00*     (2011.01)
  *G02F 1/015*    (2006.01)
  *G01N 21/552*   (2014.01)
  *G01N 21/64*    (2006.01)
  *H01L 31/06*    (2012.01)

(52) U.S. Cl.
  CPC ............ *B82Y 20/00* (2013.01); *G01N 21/648* (2013.01); *G02F 2001/0155* (2013.01); *G02F 2203/10* (2013.01); *G02F 2203/15* (2013.01); *H01L 31/06* (2013.01)

(58) Field of Classification Search
  USPC ........ 359/240, 241, 244, 245; 356/432, 445; 250/200, 338.4; 257/21; 438/57, 69, 72, 438/73, 92; 977/700, 902, 932, 948
  See application file for complete search history.

(56) References Cited

U.S. PATENT DOCUMENTS

| | | | |
|---|---|---|---|
| 8,507,890 B1 * | 8/2013 | Koppens | H01L 31/02327 257/10 |
| 8,772,890 B2 * | 7/2014 | Kukushkin | B82Y 20/00 257/428 |
| 8,848,194 B2 * | 9/2014 | Walters | B82Y 20/00 356/445 |
| 9,244,268 B2 * | 1/2016 | Long | G02F 1/0126 |
| 9,537,027 B2 * | 1/2017 | Lu | H01L 31/03521 |
| 2014/0346357 A1 * | 11/2014 | Jarrahi | H01L 31/09 250/338.4 |

\* cited by examiner

SYSTEMS FOR TUNABLE NANOCUBE PLASMONIC RESONATORS AND METHODS FOR FORMING

BACKGROUND

Resonators exhibit resonance or resonant behavior at certain frequencies, called resonant frequencies. Oscillations in a resonator can be either electromagnetic or mechanical (including acoustic). Resonators can be used to either generate waves of specific frequencies or to select specific frequencies from a signal. A plasmonic resonator couples to plasmons, which are waves associated with electromagnetic fields and electron motion near the surface of a conducting or semiconducting material. The wavelength of plasmons is typically several times smaller than the wavelength of free-space electromagnetic radiation of similar frequency, and plasmonic resonators may therefore be comprised of relatively small structures as compared to a free-space wavelength at their resonant frequency. For optical frequencies, such structures are typically tens of nanometers in size, and referred to as nanostructures (e.g., nanocubes), but similar structures and plasmon resonators may be fabricated at larger scales to operate with lower frequency plasmons, e.g., in the infrared or THz ranges. One form of plasmonic resonator is comprised of a conductive nanostructure, such as a metallic nanocube, separated from a conductive substrate by a thin (few-nm at optical frequencies) dielectric (nonconducting) gap.

SUMMARY

The present disclosure is directed to systems for tuning nanocube plasmonic resonators and methods for forming tunable plasmonic resonators. In one aspect, a first tunable plasmonic resonator system is provided. The system includes a substrate and a nanostructure positioned on a surface of the substrate. The substrate may include a semiconductor material having a carrier density. A junction is formed between the nanostructure and the substrate forming a Schottky junction. The plasmonic resonator system can be configured such that changing the carrier density distribution changes a plasmonic response of the plasmonic resonator system.

In another aspect, a second tunable plasmonic resonator system is provided. The system includes a substrate and an array of nanostructures positioned on a surface of the substrate. The substrate may include a semiconductor material having a carrier density distribution. A junction is formed between the array of nanostructures and the substrate forming an array of Schottky junctions. The system can be configured such that changing the carrier density distribution of the semiconductor material tunes a plasmonic response of at least one plasmonic resonator in the array of plasmonic resonators.

In another aspect, a third tunable plasmonic resonator system is provided. The system includes a substrate, a nanostructure, and a dielectric layer positioned between the substrate and the nanostructure. The substrate may include a semiconductor material. The semiconductor material may have a carrier density distribution. In an embodiment, the plasmonic response of the nanostructure can be controlled by varying the carrier density distribution of the semiconductor material.

In another aspect, a fourth tunable plasmonic resonator system is provided. The system includes a substrate having a semiconductor material. The system further includes an array of plasmonic resonators including an array of nanostructures and a dielectric layer positioned between the substrate and the array of nanostructures. The semiconductor material may have a carrier density distribution. In an embodiment, a plasmonic response of at least one plasmonic resonator can be controlled by varying the carrier density distribution.

In another aspect, a first method for forming a nanocube tunable plasmonic resonator is provided. The method includes forming a junction between a nanostructure and a substrate. The substrate may include a semiconductor material having a carrier density distribution and the nanostructure may be positioned on a surface of the substrate. The method further includes applying a voltage between the nanostructure and the substrate. The junction may be Schottky junction. The method further includes tuning a plasmonic response of the plasmonic resonator by changing the carrier density distribution of the semiconductor material.

In another aspect, a second method for forming an array of tunable plasmonic resonators is provided. The method includes forming a plurality of junctions between an array of nanostructures and a substrate. The substrate may include a semiconductor material having a carrier density distribution and the array of nanostructures may be positioned on a surface of the substrate. The method further includes applying a voltage between the array of nanostructures and the substrate. The junction may be a Schottky junction. The method further includes tuning a plasmonic response of at least one plasmonic resonator in the array of plasmonic resonators by changing the carrier density distribution of the semiconductor material.

In another aspect, a third method for forming a tunable plasmonic resonator is provided. The method includes forming a dielectric layer on a substrate. The substrate may include a semiconductor material having a carrier density distribution. The method further includes depositing a nanostructure on the dielectric layer of the substrate and applying a voltage between the nanostructure and the substrate. The method further includes controlling the carrier density distribution to tune a plasmonic response of the plasmonic resonator.

In another aspect, a fourth method for forming an array of tunable plasmonic resonators is provided. The method includes forming a dielectric layer on a substrate. The substrate may include a semiconductor material having a carrier density distribution. The method further includes forming an array of plasmonic resonators by depositing an array of nanostructures on the dielectric layer of the substrate. The method further includes applying a voltage between the array of nanostructures and the substrate. The method further includes controlling the carrier density distribution to tune a plasmonic response of at least one plasmonic resonator.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
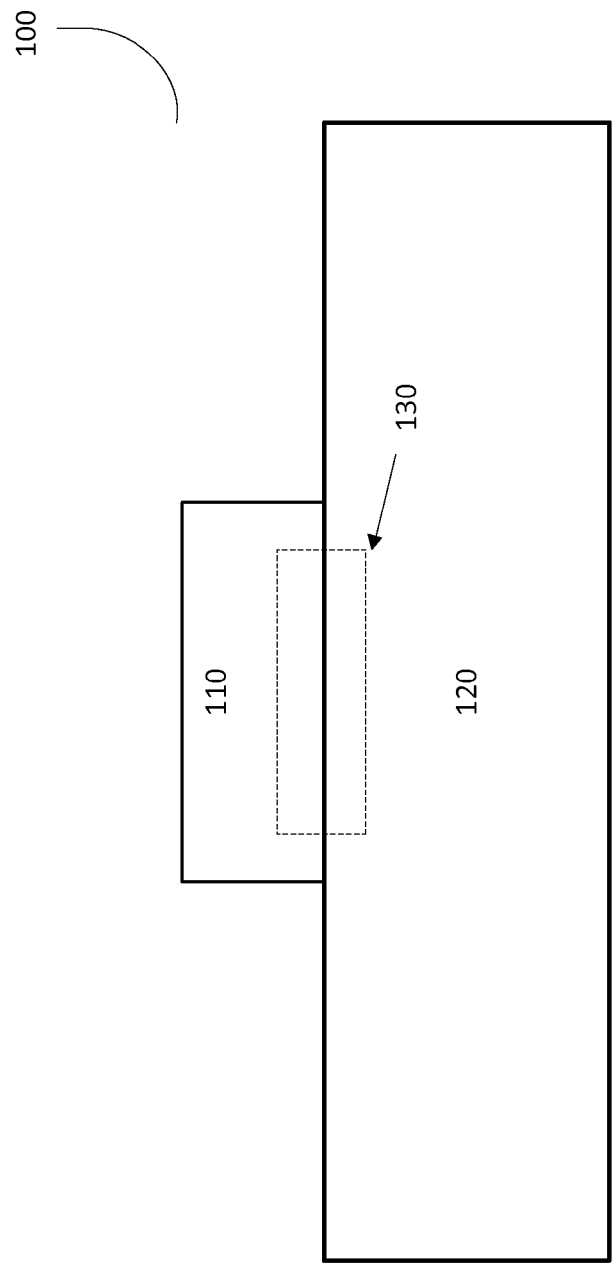
FIG. 1 is a block diagram of a nanocube tunable plasmonic resonator system in accordance with one embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the scope of the subject matter presented here.

The method and systems described herein are directed to plasmonic resonators that can be modulated using an enhancement region or a depletion region. For example, plasmonic resonators can include nanocube-on-substrate resonators, which can be controlled by varying the properties of an enhancement region or depletion region in the substrate for the resonator. A nanostructure can be formed as a switchable or controllable resonator by changing properties of a depletion region or an enhancement region positioned under the nanostructure. By altering the properties of the depletion region or the enhancement region under the nanostructure, the plasmonic properties of the nanostructure can be controlled and modulated. For a single nanocube, the plasmonic properties that can be controlled include resonant frequency and resonance strength. For an array of nanocubes, the plasmonic properties that can be controlled include an amplitude of plasmonic resonance (e.g., by changing a number of resonant nanostructures in the array or the strength of the individual resonators), the frequency of the resonance, or the width or shape of the resonance (e.g., by varying a distribution of frequencies of individual resonators).

FIG. 1 depicts tunable plasmonic resonator system 100 in accordance with one embodiment. The tunable plasmonic resonator 100 includes nanostructure 110 positioned on a surface of a substrate 120. Substrate 120 includes a semiconductor material. Between nanostructure 110 and substrate 120, junction 130 is formed that may be a Schottky junction. In some embodiments, the properties and characteristics of junction 130 may be altered to tune a plasmonic response of nanostructure 110.

Nanostructure 110 may be a structure of intermediate size between microscopic and molecular structures. For example, the thickness of nanostructure 110 may range from about 0.1 nanometer (nm) to about 100 nm. Nanostructure 110 may be of various types, shapes, and sizes, including a cube, prism, brick, or sphere. For example, in one embodiment, nanostructure 110 is a 70 nm nanocube. In some embodiments, nanostructure 110 is embedded in a fluid or solid matrix on the surface of substrate 120. Nanostructure 110 may include at least one of aluminum, silver, or gold.

The plasmonic resonator 100 may be a plasmonic nanoparticle whose electrons can couple with electromagnetic radiation of wavelengths that are far larger than the particle due to the nature of the dielectric-metal interface between the medium and the particle. When the electromagnetic field interacts with conductive electrons at the metal interface or metallic nanostructure an enhanced optical near field of sub-wavelength can be achieved. The plasmonic resonator 100 may exhibit scattering, absorbance, and coupling properties based on its geometry, composition, and position relative to the surface of substrate 120. In some embodiments, plasmonic resonators 100 may exhibit plasmonic properties. Plasmonic properties may generally refer to how an electromagnetic field interacts with the plasmonic resonator 100. For example, the plasmonic properties may include controlling what wavelengths are absorbed versus reflected by the plasmonic resonator 100. This may also be referred to as an optical response of plasmonic resonator 100. The plasmonic resonator 100 can be configured to selectively absorb at resonance frequency. In some embodiments, the properties of a region (e.g., a depletion region, a dielectric region) can be controlled to tune a reflectance spectrum of the plasmonic resonator 100 over a range of wavelengths. The plasmonic resonator can couple efficiently with electromagnetic radiation having wavelengths much larger than the dimensions of nanostructure 110, due to the interaction of the electromagnetic fields with the electric charges in the nanoparticle and in the substrate. The coupled near-field oscillations of the fields and particles are described as plasmonic oscillations. The coupling of radiation with the plasmonic oscillations affects the absorption and scattering properties of the resonator 100 when illuminated with electromagnetic radiation, and the electromagnetic emission properties if the resonator is excited by other means such as molecular transitions (fluorescent emission) within the resonator. The interaction with electromagnetic fields is enhanced at certain frequencies corresponding to resonances in the plasmonic oscillations.

Substrate 120 may include a semiconductor material having a carrier density distribution. For example, substrate 120 may include silicon. Other possible semiconductor substrates include germanium, gallium arsenide, indium gallium arsenide, gallium phosphide, indium phosphide, etc. The substrate may include intrinsic (undoped) semiconductor, or may be wholly or partially doped to control the density and distribution of free charge carriers (electrons or holes) in the substrate. In some embodiments, junction 130 is formed between nanostructure 110 and substrate 120. Junction 130 may be a Schottky junction, which produces a Schottky barrier. A Schottky barrier is a potential energy barrier for electrons, which is formed at a metal-semiconductor junction. For example, a Schottky barrier may be formed between nanostructure 110 and substrate 120, producing a narrow region in the semiconductor which is depleted of conduction electrons. This depletion region forms an insulating layer between nanostructure 110 and the bulk of the substrate 120.

In some embodiments, junction 130 is configured to allow control of the plasmonic response of plasmonic resonator 100 by changing the carrier density distribution in the semiconductor material of substrate 120. For example, the properties of nanostructure 110 can be adjusted by varying a voltage applied between nanostructure 110 and substrate 120. The voltage may be provided between nanostructure 110 and substrate 120 by a voltage source to change junction 130 from an unbiased junction to a biased junction.

In some embodiments, junction 130 may be biased to increase the width of the depletion region produced by the Schottky junction, effectively increasing the separation between nanostructure 110 and the bulk conducting region of substrate 120 and raising the resonant frequency of the nanoresonator. In some embodiments, junction 130 may be biased to decrease the width of the depletion region, effectively decreasing the separation and lowering the resonant frequency. In some embodiments, junction 130 may be biased into conduction, eliminating the depletion region and eliminating the resonant plasmonic response of resonator 100. In some embodiments, junction 130 may be reverse biased sufficiently that the depletion region width becomes large compared to the plasmon wavelength, such that nanostructure 110 is effectively decoupled from the conducting part of substrate 120 and the remaining plasmon response is approximately that of an isolated nanostructure 110.

Figure 2:
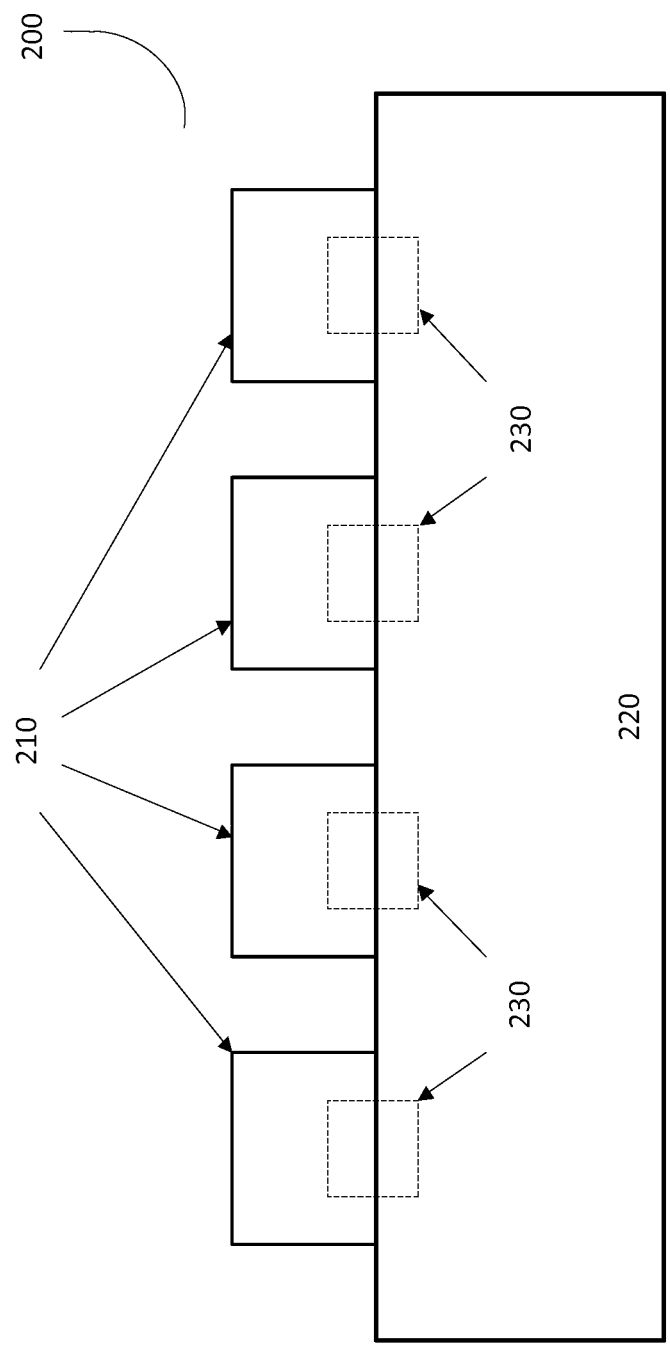
FIG. 2 is a block diagram of a nanocube tunable plasmonic resonator system according to another embodiment.

Now referring to FIG. 2, FIG. 2 shows tunable plasmonic resonator 200 according to another embodiment. Tunable plasmonic resonator 200 includes an array of nanostructures 210 positioned on a surface of substrate 220. Substrate 220 may include a semiconductor material having a carrier density distribution. Junction 230 may be formed between the array of nanostructures 210 and substrate 220. Junction 230 may be configured to tune a plasmonic response of each nanostructure 210 in the array of nanostructures 210 by changing the carrier density distribution within the semiconductor material in substrate 220.

In an embodiment, substrate 220 and junctions 230 of tunable plasmonic resonator 200 illustrated in FIG. 2 may be similar to substrate 120 and junction 130 described above with respect to tunable plasmonic resonator 100 illustrated in FIG. 1. However, tunable plasmonic resonator 200 illustrated in FIG. 2 is different from tunable plasmonic resonator 100 illustrated in FIG. 1, in that tunable plasmonic resonator 200 includes the array of nanostructures 210.

The array of nanostructures 210 may include nanostructures 210 of the same type, shape, size, and properties. In other embodiments, the array may include nanostructures 210 of varying types, shapes, sizes, and properties. For example, the array may include two or more different types of nanostructures 210, two or more different sized nanostructures 210, or two or more different shaped nanostructures 210. Each nanostructure 210 may have different optical characteristics depending on its own individual geometry.

The array of nanostructures 210 may be embedded in a fluid or a solid matrix on a surface of substrate 220. In some embodiments, the nanostructures 210 in the array may be deposited in a random formation. In other embodiments, nanostructures 210 are deposited in a patterned formation. For example, each nanostructure 210 may be spaced at a pre-determined distance from a neighboring nanostructure 210 on the surface of substrate 220. In some embodiments, nanostructures 210 may be selectively deposited on the surface of the substrate through a mask to create active and non-active areas (i.e., pixels).

The surface of substrate 220 may be coated to control the placement of nanostructures 210 on the surface. For example, the surface of substrate 220 may be selectively coated to form active and non-active areas. Nanostructures 210 may be attracted to the various areas of the surface based on the coating applied. The coating may either prevent deposition or adherence of nanostructures 210 to different areas of the surface of substrate 220. The coating can also be used to control the spacing between the nanostructures, by controlling what areas the nanostructures of the surface of substrate 220 nanostructures 210 are attracted to. In some embodiments, a transparent conductor or a transparent conductor film, such as indium tin oxide (ITO), can be applied to a surface of substrate 220 to couple nanostructures 210 to the surface of substrate 220.

Figure 3:
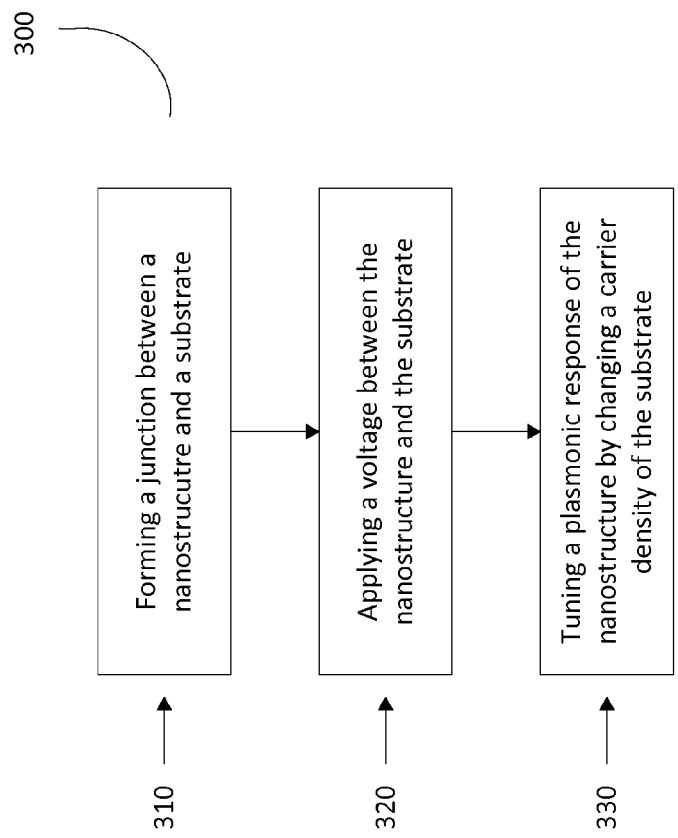
FIG. 3 is a flow diagram of a method for forming a nanocube tunable plasmonic resonator according to one embodiment.

FIG. 3 depicts a flow diagram of a method 300 for forming a nanocube tunable plasmonic resonator according to one embodiment. In brief overview, the method 300 includes forming a junction between a nanostructure and a substrate (310). The method further includes applying a voltage between the nanostructure and the substrate (320). The method further includes tuning a plasmonic response of the nanostructure by changing a carrier density distribution within the substrate (330).

In an embodiment, the junction may be formed between the nanostructure and the substrate (310). In some embodiments, the junction is a Schottky junction (e.g., Schottky barrier, Schottky diode) formed between a metal and a semiconductor material. The nanostructure may be at least one of aluminum, silver, or gold. The substrate may include a semiconductor material, such as silicon. Other possible semiconductor substrates include germanium, gallium arsenide, indium gallium arsenide, gallium phosphide, indium phosphide, etc. The semiconductor material may have a carrier density. The carrier density may refer to a measure of the density of electrons in the semiconductor material, such as the number of charge carriers per unit volume. The semiconductor may be wholly or partially doped to control the density and distribution of free charge carriers (electrons or holes) in the substrate.

To form the junction, the nanostructure may be deposited on a surface of the substrate. For example, the nanostructure may be deposited from a liquid or fluid onto the surface of the substrate. Nanostructures may also be deposited by individually being placed on the surface of the substrate, mechanically scattered on the surface of the substrate, by lithographic processes (e.g., etching), by nanoimprinting, etc. The nanostructures may be embedded in a solid or liquid after deposition.

In some embodiments, a voltage is applied between the nanostructure and the substrate (320). The voltage can be used to control the properties of the junction. The voltage may be applied using a voltage source, such as a pair of electrodes. For example, a first electrode may be coupled to a surface of the nanostructure and a second electrode may be coupled to a bottom surface of the substrate. In other embodiments, a first electrode may be coupled to a first side of the substrate and a second electrode may be coupled to a second side of the substrate.

In some embodiments, a control beam is used to control the properties of the junction. The control beam may be an electromagnetic radiation having a photon energy at or above a bandgap of the semiconductor material in the substrate. The control beam may propagate electromagnetic radiation through the nanostructure and the substrate to change properties of the junction.

The method further includes tuning a plasmonic response of the nanostructure by changing a carrier density distribution of the substrate (330). As the voltage is applied between the nanostructure and the substrate, the charge carriers in the substrate may move to the nanostructure, changing the carrier density of the substrate. By controlling the amount of voltage applied between the nanostructure and the substrate, a voltage-tunable or a voltage-switchable resonator can be created.

In some embodiments, the nanostructures are particles (e.g., plasmonic nanoparticles) whose electrons can couple with electromagnetic radiation of wavelengths that are far larger than the nanostructure due to the nature of the dielectric-metal interface between the medium and the particles. By tuning or adjusting the electron density of the nanostructure the plasmonic response or optical response of the nanostructure can be modulated. The properties of the nanostructure can be controlled using the depletion region to change or modify absorptive or reflective characteristics of the nanostructure in response to light or electromagnetic radiation. For example, in one embodiment, the resonance frequency of the nanostructure can be modulated. In some embodiments, a reflectance spectrum corresponding to the nanostructure can be tuned over a range of wavelengths.

Figure 4:
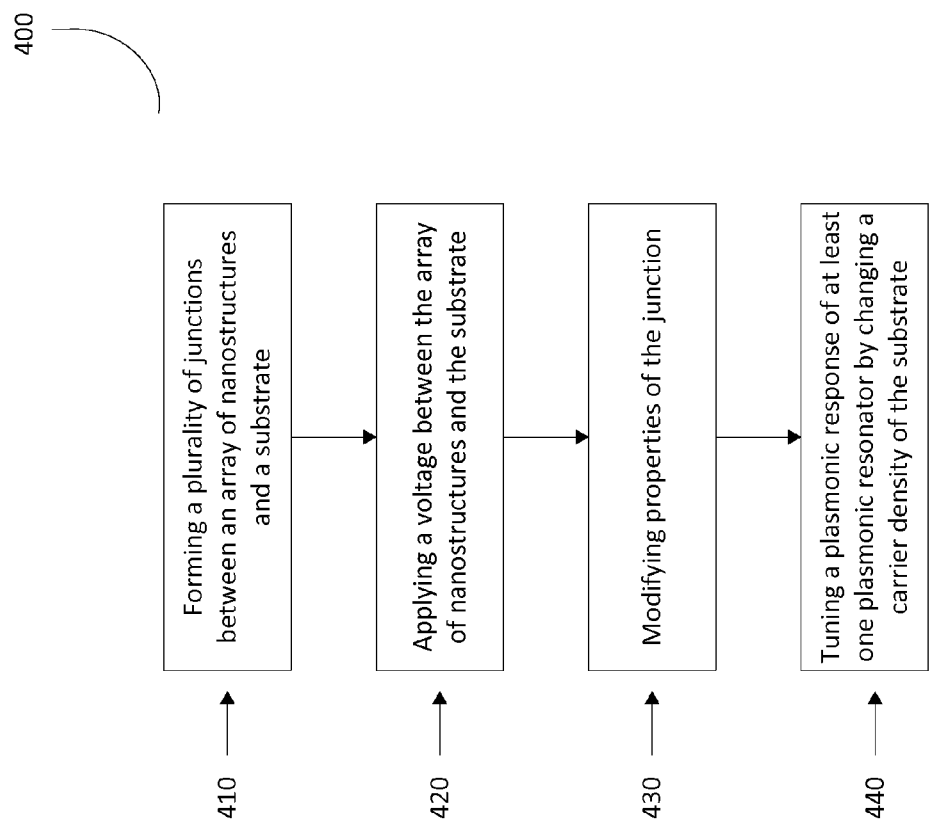
FIG. 4 is a flow diagram of a method for forming a nanocube tunable plasmonic resonator according to one embodiment.

FIG. 4 depicts a flow diagram of a method 400 for forming an array of tunable plasmonic resonators according to one embodiment. In brief overview, the method 400 includes forming a plurality of junctions between an array of nanostructures and a substrate (410). The method further includes applying a voltage between the array of nanostructures and the substrate (420). The method further includes modifying properties of the junction (430). The method further includes tuning a plasmonic response of at least one plasmonic resonator in the array of plasmonic resonators by changing a carrier density distribution of semiconductor material of the substrate (440).

A plurality of junctions (e.g., an array of junctions) may be formed between each of an array of corresponding nanostructures and a substrate (410). In some embodiments, the junction is a Schottky junction (e.g., Schottky barrier, Schottky diode) formed between a metal and a semiconductor material. The array of nanostructures may include nanostructures of the same type, size, shape, and properties. In other embodiments, the array includes nanostructures of varying type, size, shape, or properties. The nanostructures may be at least one of aluminum, silver, or gold. The substrate may include a semiconductor material, such as silicon. Other possible semiconductor substrates include germanium, gallium arsenide, indium gallium arsenide, gallium phosphide, indium phosphide, etc. The semiconductor material may have a carrier density. The carrier density may refer to a measure of the density of electrons in the semiconductor material, such as the number of charge carriers per unit volume. The semiconductor may be wholly or partially doped to control the density and distribution of free charge carriers (electrons or holes) in the substrate.

To form the junction, the array of nanostructures may be deposited on a surface of the substrate as disclosed herein. The nanostructures in the array may be positioned in a random formation. In other embodiments, the nanostructures in the array are positioned in a defined order. For example, the nanostructures may be positioned at a predetermined distance from each other.

In some embodiments, active and non-active areas (i.e., pixels) are created on the surface of the substrate using a selective placement of the nanostructures through a mask. After the nanostructures have been placed on the substrate, some nanostructures may be selectively removed to create active and non-active areas on the surface of the substrate. The surface of the substrate may be selectively coated to control placement of the nanostructures and to form active and non-active areas. The coating applied to the surface of the substrate may prevent deposition or adherence of the nanostructures to certain areas on the surface. In some embodiments, the coating may be used to control spacing of the nanostructures on the surface of the substrate. The nanostructures can be coupled to the surface of the substrate using a transparent conductor or a transparent conductor film, such as indium tin oxide (ITO).

In some embodiments, contacts may be patterned on one or both sides of the substrate to form a matrix of separately controllable areas (i.e., pixels). The nanostructures may be positioned relative to these areas, for example, to form resonators only in the central part of each controllable area, avoiding edges where electric fields and depletion thicknesses are potentially nonuniform.

In some embodiments, a voltage is applied between the array of nanostructures and the substrate (420). The voltage can be used to control the properties of the junction. The voltage may be applied using a voltage source, such as a pair of electrodes. For example, a first electrode may be coupled to a surface of the array of nanostructures and a second electrode may be coupled to a bottom surface of the substrate. In other embodiments, a first electrode may be coupled to a first side of the substrate and a second electrode may be coupled to a second side of the electrode. In some embodiments, a control beam may be used to control the properties of the junction. The control beam may be an electromagnetic radiation having a photon energy at or above a bandgap of the semiconductor material in the substrate.

The method further includes modifying properties of the junction (430). In some embodiments, the voltage can be used to change the junction from an unbiased junction to a biased junction. Biasing may refer to the ability of electrons to move from the semiconductor material, through the Schottky barrier, into a nanostructure in the array of nanostructures. In an unbiased state, no electrons move between the semiconductor material and the nanostructures in the array. In a biased state, electrons may move freely from the semiconductor material to the nanostructures. In some embodiments, the movement of electrons creates a depletion region in the semiconductor material under the various nanostructures in the array. In some embodiments, an array of depletion regions is created under the array of nanostructures.

The method further includes tuning a plasmonic response of at least one plasmonic resonator in the array of plasmonic resonators by changing a carrier density distribution within the substrate (440). As the voltage is applied between the array of nanostructures and the substrate, the charge carriers in the substrate may move to a nanostructure above a respective depletion region, changing the carrier density of the substrate. By controlling the amount of voltage applied between the nanostructures and the substrate, a voltage-tunable or a voltage switchable resonator can be created. In some embodiments, the nanostructures have varying properties and can create two or more different types of resonators having different wavelengths and/or switching properties.

Figure 5:
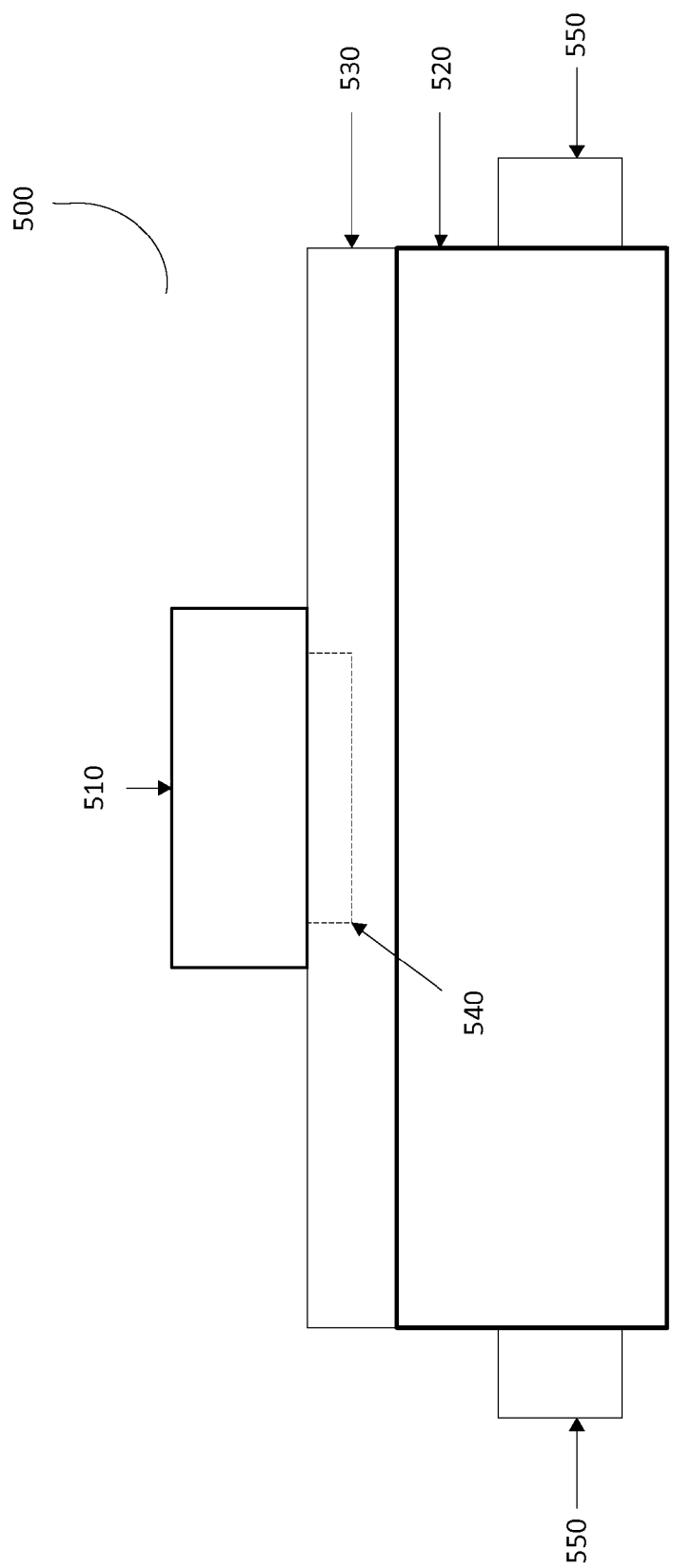
FIG. 5 is a block diagram of a tunable plasmonic resonator according to one embodiment.

Now referring to FIG. 5, tunable plasmonic resonator 500 is illustrated according to one embodiment. Tunable plasmonic resonator 500 includes nanostructure 510, substrate 520, and dielectric layer 530 positioned between nanostructure 510 and substrate 520. In some embodiments, the carrier density distribution within substrate 520 may be changed to tune a plasmonic response of nanostructure 510.

Nanostructure 510 may be a structure of intermediate size between microscopic and molecular structures. For example, the thickness of nanostructure 510 may range from about 0.1 nanometers (nm) to about 100 nm. Nanostructure 510 may be of various types, shapes, and sizes, including a cube, prism, brick, or sphere. For example, in one embodiment, nanostructure 510 is a 70 nm nanocube. In some embodiments, nanostructure 510 is embedded in a fluid or solid matrix on the surface of the substrate 520. Nanostructure 510 may include at least one of aluminum, silver, or gold. Substrate 520 includes a semiconductor material having a carrier density distribution. For example, substrate 520 may include silicon. Other possible semiconductor substrates include germanium, gallium arsenide, indium gallium arsenide, gallium phosphide, indium phosphide, etc. The substrate may be wholly or partially doped to control the density and distribution of free charge carriers (electrons or holes) near the surface of the substrate in the absence of applied voltages.

In some embodiments, dielectric layer 530 is formed on a surface of substrate 520. Dielectric layer 530 may be a few nanometers thick (e.g., less than 10 nm). In some embodiments, dielectric layer 530 includes a dielectric material that is an electrical insulator and can be polarized by an applied electric field. For example, the dielectric material may be controlled using an electric field created by voltage source 550. Voltage source 550 may include a pair of electrodes. For example, a pair of electrodes positioned adjacent to tunable plasmonic resonator 500 as illustrated in FIG. 5. In other embodiments, of the pair of electrodes, one electrode is in nanostructure 510 and one electrode is in substrate 520.

In some embodiments, the electric field is generated by incident radiation from a control beam. The control beam can be used to control the properties of dielectric layer 530. The control beam may be an incident electromagnetic radiation that propagates through nanostructure 510 and substrate 520. The control beam may include a photon energy greater than or equal to a bandgap of the semiconductor material in substrate 520.

In some embodiments, a variable or switchable enhancement region or depletion region is formed under nanostructure 510 using dielectric layer 530. For example, the depletion region may be formed in substrate 520. The generated electric field may be used to alter the properties and characteristics of substrate 520 to tune the plasmonic response of nanostructure 510. For example, the generated electric field may be used to alter a thickness of a depletion region in substrate 520 to tune the plasmonic response of nanostructure 510.

In some embodiments, substrate 520 may be formed into a metal-oxide-semiconductor (MOS) device or similar gate like structure. Gate 540 may be formed on the surface of substrate 520, for example in dielectric layer 530. Gate 540 may include a layer of metal or polycrystalline silicon deposited on top of dielectric layer 530. In some embodiments, nanostructure 510 is deposited on top of gate 540 to form a nanocube resonator. In some embodiments, substrate 520 may include circuitry components, including a complementary metal-oxide semiconductor (CMOS) logic gate, memory, or gate drivers.

Figure 6:
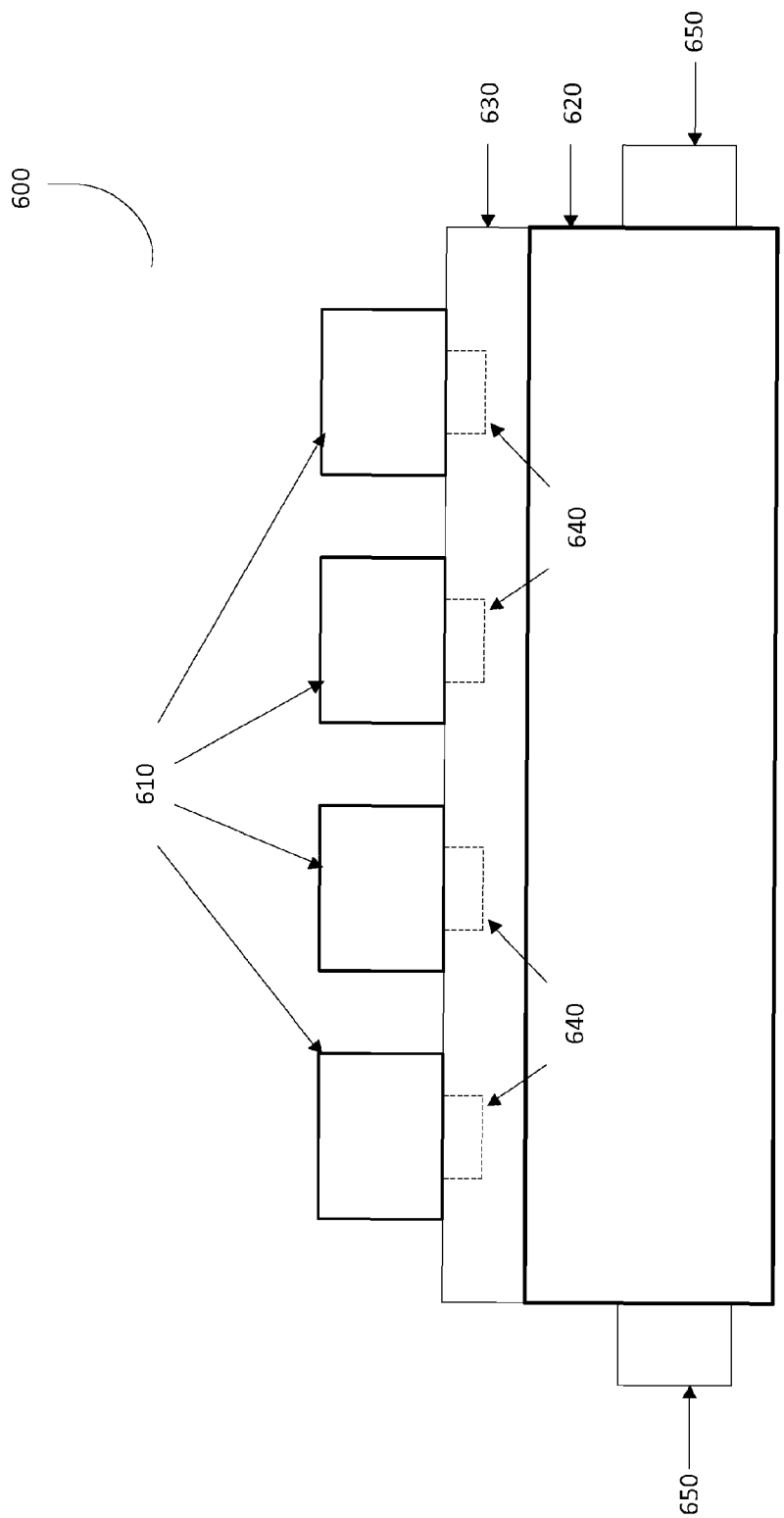
FIG. 6 is a block diagram of a tunable plasmonic resonator according to one embodiment.

Now referring to FIG. 6, tunable plasmonic resonator 600 is illustrated according to one embodiment. Tunable plasmonic resonator 600 includes an array of nanostructures 610, substrate 620, and dielectric layer 630 positioned between nanostructure 610 and substrate 620. In some embodiments, the carrier density distribution within substrate 620 is changeable to tune a plasmonic response of nanostructure 610.

In an embodiment, substrate 620 and dielectric layer 630 of tunable plasmonic resonator 600 illustrated in FIG. 6 are similar to the substrate 520 and the dielectric layer 530 described above with respect to FIG. 5. However, tunable plasmonic resonator 600 illustrated in FIG. 6 is different from the tunable plasmonic resonator 500 illustrated in FIG. 5, in that tunable plasmonic resonator 600 includes the array of nanostructures 610.

The array of nanostructures 610 may be deposited on dielectric layer 630 of the substrate 620. The array may include nanostructures 610 of the same type, with similar characteristics, such as size and shape. In some embodiments, the array includes nanostructures of varying types with different shapes and sizes. Nanostructures 610 may have different characteristics, including different resonance wavelengths.

In some embodiments, the array of nanostructures 610 may be deposited on the dielectric layer 630 in a manner similar to other deposition processes disclosed herein. Each of the nanostructures 610 in the array may be deposited in a random formation. In other embodiments, nanostructures 610 may be deposited in a patterned formation. For example, each nanostructure 610 may be deposited and spaced at a pre-determined distance from a neighboring nanostructure 610 on the surface of the dielectric layer 630.

In some embodiments, nanostructures 610 may be selectively deposited on the surface of substrate 620 through a mask. For example, nanostructures 610 may be deposited such that they are aligned with (e.g., on top of) at least one gate 640 formed into dielectric layer 630. The surface of dielectric layer 630 may be coated to control the placement of nanostructures 610 on the surface. For example, the surface of dielectric layer 630 may be selectively coated to form resonators only on gates 640. The coating may be used to prevent deposition or adherence of nanostructures 610 to areas on the surface of dielectric layer 630 not corresponding to at least one gate 640. In some embodiments, the coating is used to space nanostructures 610 such that they are spaced away from the surface and prevent formation of depletion region resonators in a frequency range of interest.

Substrate 640 may include a semiconductor material such as silicon. Dielectric layer 630 may include silicon dioxide. In some embodiments, the dielectric layer 630 has a varying thickness. For example, dielectric layer 630 may include a first dielectric region located under a first nanostructure 610 that has a first thickness. Dielectric layer 630 may also include a second dielectric region under a second nanostructure 610 having a second thickness different from the first thickness.

In some embodiments, gates 640 may be formed into dielectric layer 630. For example, substrate 620 may be formed such that is it a MOS device or similar gate like structure. An array of gates 640 may be formed into a surface of dielectric layer 630 to couple with nanostructures 610. Gates 640 may include a metal or polycrystalline silicon. In some embodiments, the array of gates 640 may include gates 640 with similar properties and characteristics. In other embodiments, the array may include gates 640 with different characteristics and properties. For example, the array may include gates 640 with different doping levels and/or thicknesses.

In some embodiments, voltage source 650 is coupled to tunable plasmonic resonator 600. In some embodiments, the carrier density distribution of substrate 620 may be controlled using an electric field created by voltage source 650. Voltage source 650 may include a pair of electrodes. For example, a pair of electrodes may be positioned adjacent to tunable plasmonic resonator 600 as illustrated in FIG. 6. Voltage source 650 can be used to control and modify a thickness of dielectric layer 630.

Figure 7:
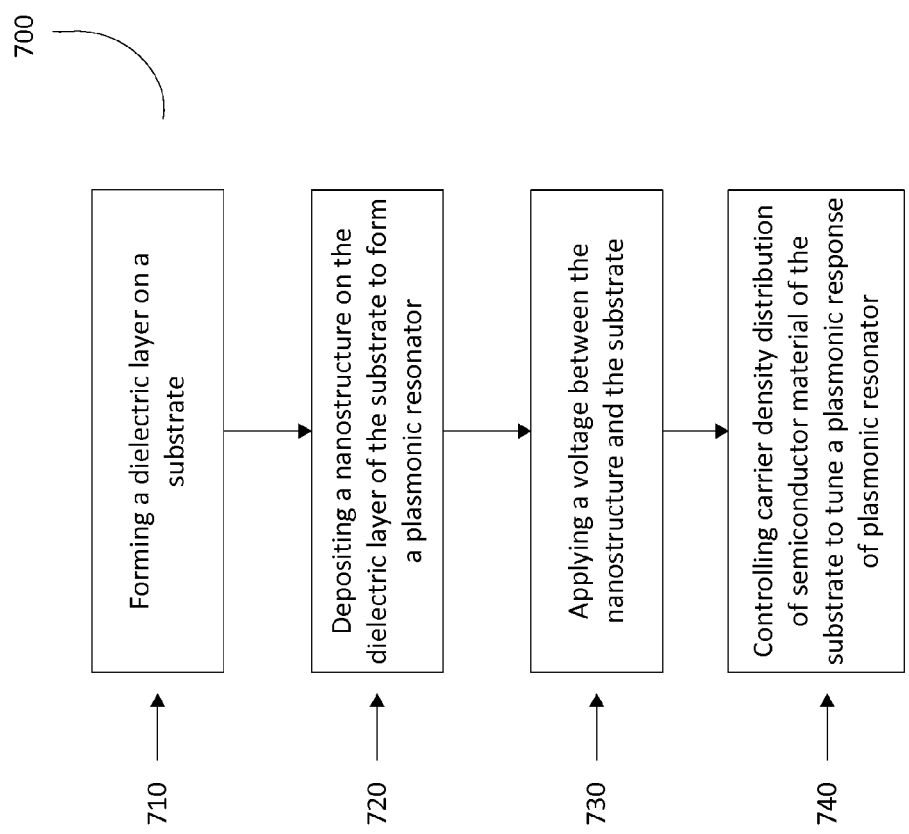
FIG. 7 is a flow diagram of a method for forming a nanocube plasmonic resonator according to one embodiment.

FIG. 7 depicts a flow diagram of a method 700 for forming a plasmonic resonator according to one embodiment. In brief overview, the method 700 includes forming a dielectric layer on a substrate (710). The method further includes depositing a nanostructure on the dielectric layer of the substrate (720). The method further includes applying a voltage between the nanostructure and the substrate (730). The method further includes controlling a carrier density distribution of semiconductor material of the substrate to tune a plasmonic response of the plasmonic resonator (740).

In some embodiments, a dielectric layer is formed in or on a substrate (710). The substrate may include a semiconductor material such as silicon. The dielectric layer may be a glass, plastic or oxides of various metals, for example silicon dioxide. The thickness of the dielectric layer may range from about 0.1 nm to about 10 nm.

In some embodiments, the substrate is formed such that it is a metal-oxide-semiconductor (MOS) device or similar gate like structure. For example, in one embodiment, a silicon dioxide dielectric layer is formed on a top surface of a silicon substrate. A layer of metal or polycrystalline silicon may then be deposited on top of the dielectric layer to serve as a conducting gate for the MOS like device. In some embodiments, the substrate may include circuitry components, including a complementary metal-oxide semiconductor (CMOS) logic gate, memory, or gate drivers.

In some embodiments, the method includes depositing a nanostructure on the dielectric layer of the substrate (720). The nanostructure may be embedded in a liquid or fluid on a surface of the dielectric layer after being deposited. The nanostructure may be selectively positioned, such as in a pre-determined position on the surface of the dielectric layer, or randomly positioned on the surface. In some embodiments, the surface of the dielectric layer may be patterned to identify a position for placement of the nanostructure.

In some embodiments, the substrate (e.g., dielectric layer) may be selectively coated to control the placement and location of the nanostructure on the surface of the dielectric layer. For example, the substrate may be selectively coated to form a resonator only over the gate. The selective coating may prevent deposition or adherence of the nanostructure at locations on the surface of the dielectric layer where there is not gate.

The method further includes applying a voltage between the nanostructure and the substrate (730). A voltage source may be used to apply a voltage or an electric field to the nanostructure and the substrate. In some embodiments, the voltage source includes a pair of electrodes. For example, in one embodiment, a first electrode is coupled to the nanostructure and the second electrode is coupled to the substrate. The pair of electrodes can apply a voltage between the nanostructure and the substrate. In other embodiments, a pair of adjacent electrodes apply an electric field to the substrate. For example, a first electrode is coupled to a first side of the substrate and a second electrode is coupled to a second side of the substrate. The pair of electrodes can generate an electric field to control and change characteristics of the substrate. The voltage can be used to control the properties of the dielectric layer of the substrate. In some embodiments, a control beam may be used to control properties of the substrate. For example, incident radiation from the control beam may be applied to the nanostructure and the substrate to change properties of the substrate.

The method further includes controlling the carrier density distribution of the semiconductor material of the substrate to tune a plasmonic response of the plasmonic resonator (740). By varying an applied voltage applied, the properties of the substrate, more specifically the enhancement region or depletion region adjacent to the surface can be controlled, including a thickness of the enhancement region or depletion region. For example, the thickness of the enhancement region or the depletion region can be altered by applying a voltage. In an embodiment, a negative voltage may be applied to a gate created on the dielectric layer and cause negatively charged conduction electrons in the semiconductor nearest the gate to be repelled by the negative charge. The negatively charged electrons may exit through a bottom contact and leave behind a depletion region. By varying the voltage applied, the carrier density distribution of the depletion region can be controlled. For example, the greater the negative charge placed on the gate, the more negative the applied gate voltage, and the more electrons that leave the semiconductor surface, enlarging the depletion region.

In some embodiments, the depletion region is formed under the nanostructure and can be used to tune plasmonic properties of the nanostructure including a plasmonic response of the nanostructure. By changing the carrier density (i.e., electron density) under the nanostructure the plasmonic properties of the nanostructure can be controlled. The plasmonic properties may generally refer to how an electromagnetic field interacts with the nanostructure. For example, the plasmonic properties may include controlling what wavelengths are absorbed versus reflected by the nanostructure. This may also be referred to as an optical response of the nanostructure. The nanostructures can be configured to selectively absorb at resonance frequency. In some embodiments, the resonance frequency of the nanostructure can be modulated. The properties of the dielectric layer can be controlled to tune a reflectance spectrum of the nanostructure over a range of wavelengths.

Figure 8:
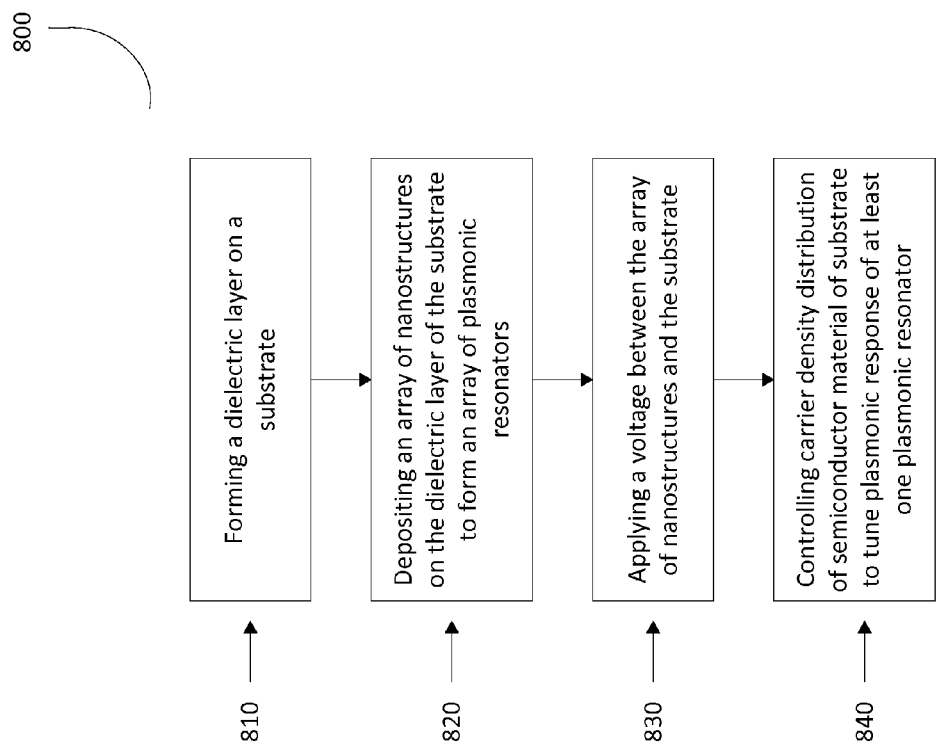
FIG. 8 is a flow diagram of a method for forming a nanocube tunable plasmonic resonator with an array of nanostructures according to one embodiment.

FIG. 8 depicts a flow diagram of a method 800 for forming a nanocube tunable plasmonic resonator with an array of nanostructures. In brief overview, the method 800 includes forming a dielectric layer on a substrate (810). The method further includes depositing an array of nanostructure on the dielectric layer of the substrate (820). The method further includes applying a voltage between the array of nanostructures and the substrate (830). The method further includes controlling a carrier density distribution of semiconductor material of the substrate to tune a plasmonic response of at least one plasmonic resonator of the array of plasmonic resonators (840).

In some embodiments, a dielectric layer is formed in or on a substrate (810). The substrate may include a semiconductor material such as silicon. Other possible semiconductor substrates include germanium, gallium arsenide, indium gallium arsenide, gallium phosphide, indium phosphide, etc. The substrate may be wholly or partially doped to control the density and distribution of free charge carriers (electrons or holes) near the surface of the substrate in the absence of applied voltages. The dielectric layer may be a glass, plastic or oxide of various metals, for example silicon dioxide. The thickness of the dielectric layer may range from about 0.1 nm to about 10 nm. In some embodiments, the dielectric layer may be formed with two or more different thicknesses.

In some embodiments, the substrate is formed such that is it a metal-oxide-semiconductor (MOS) device or similar gate like structure. For example, in one embodiment, a silicon dioxide dielectric layer is formed on a top surface of a silicon substrate. A layer of metal or polycrystalline silicon may then be deposited on top of the dielectric layer to serve as a conducting gate for the MOS like device. The substrate can be formed to create an array of gates on the surface of the dielectric layer. In some embodiments, the gate structures may have two or more different doping levels and thicknesses. In some embodiments, the substrate may include circuitry components, including a complementary metal-oxide semiconductor (CMOS) logic gate, memory, or gate drivers.

In some embodiments, the method includes depositing an array of nanostructures on the dielectric layer of the substrate to form an array of plasmonic resonators (820). In some embodiments, two or more nanostructures are deposited on the surface of the dielectric layer, such as an array of nanostructures. The array of nanostructures may include nanostructures of the same type, shape, size, and properties. In other embodiments, the array includes nanostructures of varying types, shapes, sizes, and properties. For example, the array may include two or more different types of nanostructures, two or more different sized nanostructures, or two or more different shaped nanostructures.

The nanostructures in the array may be deposited according to various processes disclosed herein. Each nanostructure in the array may be randomly spaced relative to another nanostructure on the surface of the dielectric layer. In some embodiments, the nanostructures are selectively patterned on the surface of the dielectric layer. For example, the nanostructure may be selectively positioned on one or more gates created on the dielectric layer through a mask. The nanostructures may be selectively positioned using a nanoprinting procedure or a nanoassembly procedure. The nanostructures may also be deposited uniformly on the surface, such as in a pre-defined pattern or arrangement. In some embodiments, nanostructures may be selectively removed from the surface of the dielectric layer to leave a desired density of nanostructures on the surface or on gates.

In some embodiments, the substrate (e.g., dielectric layer) may be selectively coated to control the placement and location of nanostructures on the surface of the dielectric layer. For example, the substrate may be selectively coated to form resonators only over gates. The selective coating may prevent deposition or adherence of the nanostructures to locations on the surface of the dielectric layer where there is not gate.

The method further includes applying a voltage between the array of nanostructures and the substrate (830). A voltage source may be used to apply a voltage or an electric field to the array of nanostructures and the substrate. In some embodiments, the voltage source includes a pair of electrodes. For example, in one embodiment, a first electrode is coupled to the array of nanostructures and a second electrode is coupled to the substrate. The pair of electrodes can apply a voltage between the array of nanostructures and the substrate. In other embodiments, a pair of adjacent electrodes can apply an electric field to the substrate. For example, a first electrode is coupled to a first side of the substrate and a second electrode is coupled to a second side of the substrate. The pair of electrodes can generate an electric field to control and change characteristics of the substrate. The voltage can be used to control the properties of the dielectric layer of the substrate. In some embodiments, a control beam may be used to control properties of the substrate. For example, incident radiation from the control beam may be applied to the array of nanostructures and the substrate to change properties of the substrate.

The method further includes controlling a carrier density distribution of semiconductor material of the substrate to tune a plasmonic response of at least one plasmonic resonator (840). By varying a voltage applied, the properties of the substrate, more specifically the enhancement region or depletion region adjacent to the surface can be controlled, including a thickness of the enhancement region or the depletion region. For example, the thickness of the depletion region can be altered by applying a voltage. The voltage can change a carrier density distribution of the substrate. In an embodiment, a negative voltage may be applied to a gate created on the dielectric layer and cause negatively charged conduction electrons in the semiconductor nearest the gate to be repelled by the negative charge. The negatively charged electrons may exit through a bottom contact and leave behind a depletion region. By varying the voltage applied, the carrier density distribution of the depletion region can be controlled. For example, the greater the negative charge placed on the gate, the more negative the applied gate voltage, and the more electrons that leave the semiconductor surface, enlarging the depletion region.

In some embodiments, an array of depletion regions is formed under each of the nanostructures and can be used to tune plasmonic properties of each nanostructure including a plasmonic response of each nanostructure. By changing the carrier density distribution (e.g., distribution of charge carries such as electrons) under the nanostructure the plasmonic properties of each nanostructure can be controlled. In some embodiments, the nanostructures in the array may have varying properties. For example, the array of nanostructures may form two or more different types of resonators (e.g., center wavelengths). The resonators may be formed on two or more different sized or shaped nanostructures.

As stated above, the gate structures and dielectric layers in an array of controllable depletion regions may have varying characteristics. In some embodiments, the gate structures have two or more different doping levels and thicknesses. For example, a first depletion region under a first gate structure may have a different thickness due to an applied voltage than a second depletion region under a second gate structure.

The construction and arrangement of the systems and methods as shown in the various embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the embodiments without departing from the scope of the present disclosure.

The present disclosure contemplates methods, systems and program products on any machine-readable media for accomplishing various operations. The embodiments of the present disclosure may be implemented or modeled using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures may show a specific order of method steps, the order of the steps may differ from what is depicted. Also two or more steps may be performed concurrently or with partial concurrence. All such variations are within the scope of the disclosure. Likewise, software implementations could be accomplished with standard programming techniques with rule-based logic and other logic to accomplish the various connection steps, processing steps, comparison steps and decision steps.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed is:

1. A tunable plasmonic resonator system comprising:
a substrate, wherein the substrate includes a semiconductor material having a carrier density distribution,
a nanostructure positioned on a surface of the substrate; and
a junction formed between the nanostructure and the substrate forming a Schottky junction;
wherein changing the carrier density distribution of the semiconductor material changes a plasmonic response of the plasmonic resonator system.

2. The system of claim 1, wherein the semiconductor material includes one of silicon, germanium, gallium arsenide, indium gallium arsenide, gallium phosphide, or indium phosphide.

3. The system of claim 1, further comprising a voltage source, wherein the voltage source is configured to provide a voltage between the substrate and the nanostructure.

4. The system of claim 3, wherein the junction is configurable as one of a biased junction or an unbiased junction dependent on the voltage between the substrate and the nanostructure.

5. The system of claim 4, wherein a plasmonic resonance of the nanostructure is variable based on the voltage applied between the nanostructure and the substrate.

6. The system of claim 1, wherein the plasmonic response of the system corresponds to a response to an incident light.

7. The system of claim 1, wherein tuning the plasmonic response changes a resonance wavelength of the nanostructure.

8. The system of claim 1, wherein tuning the plasmonic response changes an absorption spectrum of the system.

9. The system of claim 1, wherein tuning a plasmonic resonance of the nanostructure modifies a reflectance spectrum of the nanostructure.

10. The system of claim 1, wherein the nanostructure is embedded in a fluid or solid matrix on the surface of the substrate.

11. The system of claim 1, wherein the nanostructure includes at least one of aluminum, silver, or gold.

12. The system of claim 1, wherein the nanostructure includes a nanocube.

13. A tunable plasmonic resonator system, comprising:
a substrate, wherein the substrate includes a semiconductor material having a carrier density distribution,
an array of plasmonic resonators comprising an array of nanostructures positioned on a surface of the substrate; and
a plurality of junctions formed between each of the array of nanostructures and the substrate forming a plurality of Schottky junctions;
wherein changing the carrier density distribution of the semiconductor material tunes a plasmonic response of at least one plasmonic resonator in the array of plasmonic resonators.

14. The system of claim 13, wherein the semiconductor material includes one of silicon, germanium, gallium arsenide, indium gallium arsenide, gallium phosphide, or indium phosphide.

15. The system of claim 13, further comprising a voltage source, wherein the voltage source is configured to provide a voltage between the substrate and the array of nanostructures.

16. The system of claim 15, wherein each junction is configurable as one of a biased junction or an unbiased junction dependent on the voltage between the substrate and the array of nanostructures.

17. The system of claim 16, wherein the plasmonic response of each plasmonic resonator is adjustable by varying the voltage applied between the array of nanostructures and the substrate.

18. The system of claim 13, wherein the plasmonic response of the at least one plasmonic resonator corresponds to a response to an incident light.

19. The system of claim 13, wherein tuning the plasmonic response changes an absorption spectrum of at least one nanostructure.

20. The system of claim 13, wherein tuning the plasmonic response changes a resonance wavelength of at least one nanostructure.

21. The system of claim 20, wherein each junction is configured to modify a reflectance spectrum of the at least one nanostructure.

22. The system of claim 13, wherein the array of nanostructures is embedded in a fluid or solid matrix on the surface of the substrate.

23. The system of claim 13, wherein each nanostructure in the array of nanostructures includes at least one of aluminum, silver, or gold.

24. The system of claim 13, wherein at least one nanostructure in the array of nanostructures is a nanocube.

25. A tunable plasmonic resonator system, comprising:
a substrate, wherein the substrate includes a semiconductor material having a carrier density distribution;
a nanostructure coupled to the substrate; and
a dielectric layer positioned between the substrate and the nanostructure;

wherein a plasmonic response of the nanostructure is variable based on varying the carrier density distribution of the semiconductor material.

26. The system of claim 25, further comprising a voltage source, wherein the voltage source is configured to provide a voltage between the substrate and the nanostructure.

27. The system of claim 26, wherein the voltage source includes a pair of electrodes positioned adjacent to the substrate.

28. The system of claim 25, wherein the properties of the dielectric layer are adjustable by varying the voltage applied between the nanostructure and the substrate.

29. The system of claim 28, wherein a thickness of the dielectric layer is adjustable by varying the voltage applied between the nanostructure and the substrate.

30. The system of claim 25, wherein the plasmonic response of the nanostructure corresponds to a response to an incident light.

31. The system of claim 25, wherein varying the carrier density distribution changes an absorption spectrum of the nanostructure.

32. The system of claim 25, wherein varying the carrier density distribution changes a resonance wavelength of the nanostructure.

33. The system of claim 25, wherein varying the carrier density distribution modifies a reflectance spectrum of the nanostructure.

34. The system of claim 25, wherein the nanostructure is embedded in a fluid or solid matrix on a surface of the substrate.

35. The system of claim 25, wherein the nanostructure includes at least one of aluminum, silver, or gold.

* * * * *